United States Patent [19]

Fujisawa et al.

[11] Patent Number: 4,526,710

[45] Date of Patent: Jul. 2, 1985

[54] LIQUID DETERGENT COMPOSITION

[75] Inventors: Noriyoshi Fujisawa, Sakura; Katsuaki Ooshima, Tokyo; Junko Iijima; Katsuhiko Deguchi, both of Matsudo, all of Japan

[73] Assignee: Kao Corporation, Tokyo, Japan

[21] Appl. No.: 446,036

[22] Filed: Dec. 1, 1982

[30] Foreign Application Priority Data

Dec. 14, 1981 [JP] Japan ................. 56-201354

[51] Int. Cl.³ ................. C11D 1/34; C11D 1/75
[52] U.S. Cl. ................. 252/545; 252/541; 252/544; 252/547; 252/117; 252/DIG. 14
[58] Field of Search ............... 252/DIG. 14, 545, 547, 252/541, 544, 117

[56] References Cited

U.S. PATENT DOCUMENTS 3,533,955 10/1970 Pader et al. ............. 252/153
4,132,679 1/1979 Tsutsumi et al. ........ 252/DIG. 14
4,369,134 1/1983 Deguchi et al. ......... 252/547

FOREIGN PATENT DOCUMENTS 993044 5/1965 United Kingdom .

*Primary Examiner*—Paul Lieberman
*Assistant Examiner*—Hoa Van Le
*Attorney, Agent, or Firm*—Oblon, Fisher, Spivak, McClelland & Maier

[57] ABSTRACT

Disclosed is a liquid detergent composition which comprises the following three ingredients: (a) an alkanolamine salt of phosphoric ester represented by the formula (I) or (II)

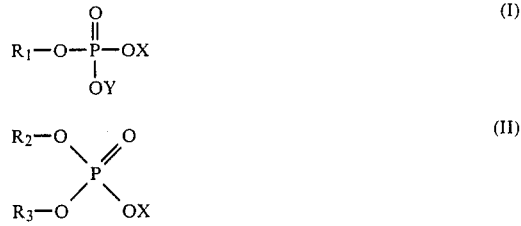

(b) an alkanolamine salt of a higher fatty acid, the alkanolamine having an alkyl group whose carbon atoms are 2 or 3 in number, and (c) an alkylamine oxide which has a hydrocarbon group having 10–14 carbon atoms.

1 Claim, No Drawings

LIQUID DETERGENT COMPOSITION

BACKGROUND OF THE INVENTION (i) Field of the Invention

This invention relates to a novel liquid detergent composition and has as its object the provision of a liquid detergent composition which is mild to the skin and is high in foaming property.

(ii) Description of the Prior Art

In recent years, there is highly required harmlessness against various detergents, and developments of novel surfactants which are high in safety are demanded with extensive studies being prosecuted thereon. On the other hand, studies have been made from a different angle to obtain highly innoxious detergents, in which among surfactants which were scarecely used because of their relatively poor detergency, there are picked up those which are highly innoxious. These surfactants are used in combination with other types of surfactants to improve their detergency effect.

Among a diversity of known surfactants, anionic surface active agents of phosphoric esters such as lauryl phosphate, myristyl phosphate and the like are mild to the skin and excellent in feeling to the touch, so that they are frequently used as a substrate for various detergent compositions. However, the detergent compositions using the esters have the disadvantage in that though satisfactory in detergency, they are very poor in foaming property.

SUMMARY OF THE INVENTION

We have made the intensive study to improve properties of detergent compositions which make use of anionic phosphate surface active agents which are highly innoxious and particularly mild to the skin. As a result, it has been found that when phosphoric ester salts having a specific type of ion pair are used in combination with alkanolamine salts of higher fatty acids and alkylamine oxides, the detergency and foaming characteristics are remarkably improved.

The present invention is based on the above finding and provides a liquid detergent composition which comprises the following three ingredients:

(a) an alkanolamine salt of phosphoric ester represented by the general formula (I) or (II)

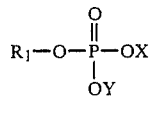

(I)

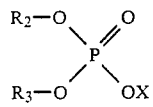

(II)

in which $R_1$, $R_2$, and $R_3$ are independently a hydrocarbon group having 8-18 carbon atoms, X represents an alkanolamine which has a hydroxyalkyl group having 2 or 3 carbon atoms, and Y represents an hydrogen atom or has the same meaning as X;

(b) an alkanolamine salt of a higher fatty acid, the alkanolamine having a hydroxyl group containing 2 or 3 carbon atoms; and (c) an alkylamine oxide which has a hydrocarbon group having 10-14 carbon atoms.

DETAILED DESCRIPTION OF THE INVENTION AND PREFERRED EMBODIMENT

The salts of phosphoric esters and alkanolamines of the ingredient (a) are those represented by the general formula (I) or (II), among which those of the formula in which $R_1$, $R_2$, and $R_3$ are independently an alkyl group having 10-14 carbon atoms, and X and Y independently represent ethanolamine and particularly triethanolamine are preferably used. The most preferable examples include mono- or di-lauryl phosphate triethanolamine, mono- or di-myristyl phosphate triethanolamine and the like. The phosphoric monoester alkanolamine represented by the formula (I) and the phosphoric diester alkanolamine represented by the formula (II) may be used singly or in combination. Preferably, there is used a combination of the phosphoric monoester alkanolamine (I) and the phosphoric diester alkanolamine (II) at a ratio by weight of 100:0-50:50, preferably 100:0-70:30. This ingredient (a) is compounded in the liquid detergent composition in an amount of 5-60 wt % (hereinafter referred to simply as %), preferably 10-50%.

The higher fatty-acid alkanolamine salts of the ingredient (b) can be represented by the general formula (III)

in which $R_4$ represents a hydrocarbon group having 9-13 carbon atoms and X has the same meaning as defined before. Preferable salts are those of the formula in which R is an alkyl group having 9-13 carbon atoms and X is ethanolamine and preferably triethanolamine. These higher fatty acid alkanolamine salts may be used singly or in combination of two or more and are used in an amount of 0.5-10%, preferably 2-5%, of the liquid detergent composition.

The ingredients (a) and (b) may be compounded in the composition as alkanolamine salts, or phosphoric esters (of the acid type) and higher fatty acids, and alkanolamine may be separately added to the system in which the salt or salts are formed.

The alkylamine oxides of the ingredient (c) can be represented, for example, by the general formula (IV)

in which $R_5$ represents a hydrocarbon group having 10-14 carbon atoms, and $R_6$ and $R_7$ independently represent methyl or ethyl group.

The preferable oxides of the formula are those in which $R_5$ is an alkyl group having 10-14 carbon atoms and $R_6$ and $R_7$ are independently methyl group. These alkylamine oxides may be used singly or in combination sand are used in an amount of 0.5-10%, preferably 1-8%, of the liquid detergent composition.

The liquid detergent composition of the invention can be prepared by dissolving or dispersing the three ingredients in a solvent such as water. In the practice of the invention, part of the alkanolamine or hydrogen which is an ion pair of the ingredients (a) and (b) may be replaced by an ion pair such as an alkali metal salt in a range not impeding the effect of the invention. In this connection, however, better results are obtained when the other ion pair is not used. The pH of the composition is conveniently in the range 6–10.5, preferably 6.5–8.5, when an aqueous 5% solution is used.

much more excellent in lathering performance than the others.

TABLE 1

| Ingredient (%) | 1 | 2 | 3* | 4* | 5* | 6 | 7 | 8 | 9 | 10 |
|---|---|---|---|---|---|---|---|---|---|---|
| Monolauryl phosphate triethanolamine | 30 | 30 | 30 | 30 | 30 | 30 | 30 | 30 | 30 | 30 |
| Dimyristyl phosphate triethanolamine | 5 | 5 | 5 | 5 | 5 | 5 | 5 | 5 | 5 | 5 |
| Triethanolamine laurate | — | 2 | 2 | — | 2 | 2 | 2 | 2 | — | — |
| Triethanolamine myristate | — | — | — | 3 | — | — | — | — | — | — |
| Lauryldimethylamine oxide | — | — | 3 | 3 | — | — | — | — | 3 | — |
| Myristyldimethylamine oxide | — | — | — | — | 5 | — | — | — | — | 5 |
| 2-alkyl-N—carboxymethyl-N—hydroxyethyl-imidazolyl betaine | — | — | — | — | — | 5 | — | — | — | — |
| 2-alkyl-N—carboxyethyl-N—hydroxyethyl-imidazolium betaine | — | — | — | — | — | — | 5 | — | — | — |
| Diethanolamide laurate | — | — | — | — | — | — | — | 5 | — | — |
| Water | balance | balance | balance | balance | balance | balance | balance | balance | balance | balance |
| Lathering Test 1 | 0.7 | 1.1 | 3.7 | 3.2 | 3.0 | 1.7 | 1.5 | 1.4 | 1.4 | 1.3 |
| Lathering Test 2 | 125 | 139 | 253 | 240 | 235 | 168 | 152 | 151 | 159 | 142 |

(*Products of the Invention)

Aside from the above ingredients, the liquid detergent composition of the invention may be admixed with ordinarily employed ingredients such as, for example, other types of surfactants, viscosity modifiers, inorganic or organic salts, wetting agents, chelating agents, preservatives, solubility aids, bactericides, colorants, pigments, pearling agents, emulsifiers, polymeric compounds, perfumes, antiphlogistics and the like within ranges not impeding the effect of the invention.

The liquid detergent composition of the invention as described above is mild to the skin and excellent in foaming characteristic, presenting very fine and affluent lathers.

The present invention is described by way of examples, which should not be construed as limiting the invention.

EXAMPLE 1

Liquid detergent compositions of the formulations indicated in Table 1 were prepared and their foaming or lathering performance was determined.

(1) Evaluation Method

Lathering Test 1

Each liquid detergent composition was tested by a hand-washing method in which it was directly applied to 20 expert panels on their hands and the degree of lathering was evaluated by the following criterion.
4: Very Good
3: Good
2: Moderate
1: Bad
0: Very bad Lathering Test 2

A reversing agitator (reversing at intervals of 5 seconds) was provided to agitate a test solution (100 ml of a 20% solution of each liquid detergent composition to which 1% of an aritificial sebum, 40° C.) in a glass cylinder (diameter 64.5 mm) at 1,000±50 rpm for 30 seconds. Thereafter, a volume of lathers were measured. The hardness of used water was 4° DH. In the table, the volume of lathers is indicated by ml.

(2) Results

The results are just as shown in Table 1. From the results, it will be seen that the products of the invention (sample Nos. 3–5) comprising the ingredients (a)–(c) are

EXAMPLE 2

(Face Washing Lotion)

| Monolauryl phosphate triethanolamine | 27 | (%) |
|---|---|---|
| Triethanolamine laurate | 5 | |
| Lauryldimethylamine oxide | 4 | |
| Carboxyvinyl polymer | 0.2 | |
| Glycerine | 8 | |
| Sorbitol | 2 | |
| Water | Balance | |

The face-washing lotion of the above formulation was mild to the skin and its lathering property 1 determined in the same manner as in Example 1 was found to be 3.6, showing fine, affluent lathering.

EXAMPLE 3

(Body Shampoo)

| Monolauryl phosphate triethanolamine | 36 | (%) |
|---|---|---|
| Triethanolamine laurate | 1 | |
| Triethanolamine myristate | 2 | |
| Lauryldimethylamine oxide | 2 | |
| Myristyldiethylamine oxide | 0.5 | |
| Cationized cellulose | 0.1 | |
| Propylene glycol | 10 | |
| Water | Balance | |

The body shampoo of the above formulation was evaluated by 20 expert panels (same as in Example 1) using towels, revealing that the lathering property 1 (according to the same criterion as in Example 1) was found to be 3.1 with affluent creamy lathering.

What is claimed is:

1. A liquid detergent composition comprising the following three ingredients:
   (a) an alkanolamine salt of phosphoric ester represented by the general formula (I) or (II)

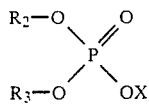 (II)

in which $R_1$, $R_2$, and $R_3$ independently represent a hydrocarbon group having 8-18 carbon atoms, X represents an alkanolamine which has a hydroxyalkyl group having 2 or 3 carbon atoms, and Y represents an hydrogen atom or has the same meaning as X;

(b) an alkanolamine salt of a higher fatty acid, the alkanolamine having an alkyl group whose carbon atoms are 2 or 3 in number; and (c) an alkylamine oxide which has a hydrocarbon group having 10-14 carbon atoms, wherein ingredient (a) is in the range of 10-60% by weight, ingredient (b) is in the range of 0.5-10% by weight and ingredient (c) is in the range of 1-8% by weight.

* * * * *